United States Patent
King et al.

(10) Patent No.: US 10,066,083 B2
(45) Date of Patent: Sep. 4, 2018

(54) FLAME-RETARDANT POLYALLYL AND POLYALKENYL ISOCYANURATE COMPOUNDS

(71) Applicant: International Business Machines Corporation, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/659,895

(22) Filed: Jul. 26, 2017

(65) Prior Publication Data

US 2018/0155530 A1 Jun. 7, 2018

Related U.S. Application Data

(63) Continuation of application No. 15/370,808, filed on Dec. 6, 2016.

(51) Int. Cl.
*C07F 9/00* (2006.01)
*C08K 5/521* (2006.01)
(Continued)

(52) U.S. Cl.
CPC .............. *C08K 5/521* (2013.01); *C07F 9/098* (2013.01); *C08K 5/0025* (2013.01); *C08K 5/0066* (2013.01)

(58) Field of Classification Search
CPC .... C07F 9/65211; C07D 251/34; C07D 25/36
See application file for complete search history.

(56) References Cited

U.S. PATENT DOCUMENTS 3,838,124 A * 9/1974 Matzner .................... C02F 5/14
544/214
4,145,544 A * 3/1979 Kuehn .................... C08F 20/36
544/193
(Continued)

FOREIGN PATENT DOCUMENTS

JP 08231847 A 9/1996
JP 2003160726 A 6/2003

OTHER PUBLICATIONS

Hwang et al., "Low Dielectric and Flame-Retardant Properties of Thermosetting Redistributed Poly(phenylene oxide)," Journal of Vinyl & Additive Technology, Mar. 2009, pp. 54-59, vol. 15, Issue 1, Published online in Wiley InterScience, 2009. DOI: 10.1002/vnl. 20176.
(Continued)

*Primary Examiner* — Robert C Boyle
(74) *Attorney, Agent, or Firm* — Nathan M. Rau

(57) ABSTRACT

Phosphate-based polyallyl isocyanurate cross-linker compounds, polyalkenyl isocyanurate cross-linker compounds, and a flame-retardant resin are disclosed. The phosphate-based polyallyl isocyanurate compound can have allyl phosphate substituents with variable functional groups. The phosphate-based polyallyl isocyanurate compound can have three or six allyl phosphate substituents. The brominated polyalkenyl isocyanurate compound can have brominated alkene-terminated substituents. The brominated alkene-terminated substituents can have variable functional groups and variable chain lengths. Both the phosphate-based polyallyl isocyanurate compounds and the brominated polyalkenyl isocyanurate compounds can be cross-linkers for epoxide polymers, acrylate polymers, vinylbenzene-terminated poly(phenyleneoxide) polymers, etc. The phosphate-based polyallyl isocyanurate compounds and the brominated polyalkenyl isocyanurate compounds can also be flame-retar-
(Continued)

dant. The flame-retardant resin can contain the phosphate-based polyallyl isocyanurate compounds or the brominated polyalkenyl isocyanurate compounds, and it can be incorporated into a printed circuit board laminate.

2 Claims, 8 Drawing Sheets

(51) Int. Cl.
*C07F 9/09* (2006.01)
*C08K 5/00* (2006.01)

(56) References Cited

U.S. PATENT DOCUMENTS

| | | | | |
|---|---|---|---|---|
| 4,200,749 | A | * | 4/1980 | Flagg ............... A01N 43/64 544/221 |
| 4,648,843 | A | * | 3/1987 | Mitra ............... A61K 6/0017 106/35 |
| 4,962,168 | A | | 10/1990 | Hiratsuna et al. |
| 7,288,587 | B2 | | 10/2007 | Saitou et al. |
| 9,447,238 | B2 | | 9/2016 | Gao et al. |
| 9,505,926 | B2 | | 11/2016 | Togawa et al. |
| 2002/0072585 | A1 | | 6/2002 | Chiu et al. |
| 2009/0048377 | A1 | * | 2/2009 | Kanno ............... C08K 5/0066 524/117 |
| 2013/0115472 | A1 | | 5/2013 | Yu et al. |
| 2013/0334477 | A1 | * | 12/2013 | Taketani ............... C08F 226/06 252/609 |
| 2014/0138128 | A1 | | 5/2014 | Chang et al. |
| 2015/0105505 | A1 | | 4/2015 | He et al. |
| 2016/0145275 | A1 | | 5/2016 | Boday et al. |
| 2016/0244607 | A1 | | 8/2016 | Kagumba et al. |
| 2016/0264761 | A1 | | 9/2016 | Timberlake et al. |

OTHER PUBLICATIONS

"TAIC® Triallyl Isocyanurate," Product Catelog, Nippon Kasei Chemical Co., Ltd., Printed: Oct. 17, 2016, 1 page. www.nkchemical.co.jp/ver_03/english/product_e/nkc_taic_e.pdf.

"Triallyl Isocyanurate (TAIC)," Products, Laizhou City Laiyu Chemical Co., Ltd., Printed: Oct. 17, 2016, 3 pages. http://chemical-laiyu.com/product-7-triallyl-isocyanurate-taic-en/139118.

"MEGTRON 6," Panasonic Product, Printed: Dec. 6, 2016, 2 pages. http://www.matrixelectronics.com/products/panasonic/megtron-6/.

King et al., "Flame-Retardant Polyallyl and Polyalkenyl Isocyanurate Compounds," U.S. Appl. No. 15/370,808, filed Dec. 6, 2016.

List of IBM Patents or Patent Applications Treated as Related, Signed Jul. 26, 2017, 2 pages.

* cited by examiner

FLAME-RETARDANT POLYALLYL AND POLYALKENYL ISOCYANURATE COMPOUNDS

BACKGROUND

The present disclosure relates to compounds for use in printed circuit board laminates and, more specifically, flame-retardant polyallyl and polyalkenyl isocyanurate compounds.

Printed circuit boards (PCBs) support and connect electronic components using features that have been etched from copper sheets, which are laminated onto a non-conductive substrate. The laminates used in PCBs are manufactured by curing layers of cloth or paper with resins. Many of the resins are formed by combining a polymer, a cross-linker, and a flame-retardant compound. The type of polymer, cross-linker, and flame-retardant compound can be selected based upon the desired characteristics of the laminate.

SUMMARY

Various embodiments are directed to phosphate-based polyallyl and polyalkenyl isocyanurate cross-linker compounds. The phosphate-based polyallyl isocyanurate compound can have a variable number of allyl phosphate substituents, each having a functional group ($R_2$) in addition to its allyl group. The $R_2$ functional group can be an allyl, a methyl, an ethyl, a propyl, an isopropyl, a phenyl, a tolyl, an anisolyl, or a benzyl. The phosphate-based polyallyl isocyanurate compound can have three allyl phosphate substituents, or it can have six allyl phosphate substituents. Additional embodiments are directed to a brominated polyalkenyl isocyanurate compound. The brominated polyalkenyl isocyanurate compound can have brominated alkene-terminated substituents. The brominated alkene-terminated substituents can have variable functional groups ($R_1$) and variable chain lengths. Both the phosphate-based polyallyl isocyanurate compounds and the brominated polyalkenyl isocyanurate compounds can be cross-linkers for epoxide polymers, acrylate polymers, vinylbenzene-terminated poly(phenyleneoxide) polymers, etc. The phosphate-based polyallyl isocyanurate compounds and the brominated polyalkenyl isocyanurate compounds can also be flame-retardant. A resin containing the phosphate-based polyallyl isocyanurate compounds or the brominated polyalkenyl isocyanurate compounds can be incorporated into a printed circuit board laminate.

DETAILED DESCRIPTION

Printed circuit boards (PCBs) are electrical circuits that can be found in virtually every type of electronic device. Electrical components of a device are mechanically supported and electronically connected by the PCB. A PCB is formed by etching a copper conductive layer laminated onto an insulating substrate. The insulating substrate can be a laminate comprising a resin and a fiber. Examples of fibers used in PCB laminates include various types of paper and fiberglass. The resin used in a laminate is made from a polymer and a cross-linker, which forms bonds between polymer chains, linking the chains together. Additionally, a flame-retardant compound is added to the resin. Flame-retardant compounds are added to resins in order to prevent PCBs from catching fire when exposed to high temperature environments or electrical power overloads.

Though flame retardancy helps ensure the safety of PCBs, many flame-retardant compounds are harmful to humans and the environment. Further, flame-retardant compounds that are added to resins can leach into the environment because they are not bound to the resin's polymer. Disclosed herein are flame-retardant compounds that may form a bond with a resin polymer. In some embodiments, the flame-retardant compounds form cross-linking bonds between two or more resin polymers, thereby forming flame-retardant cross-linking compounds. Because the cross-linkers are bound to the polymer, the cross-linkers do not leach out of the resin. Additionally, the presence of flame-retardant cross-linkers removes the necessity of adding a separate flame-retardant compound, simplifying the manufacture of the resin.

The flame-retardant cross-linkers of the present disclosure are phosphate-based polyallyl isocyanurate compounds and brominated polyalkenyl compounds. Each polyallyl and polyalkenyl isocyanurate compound discussed herein has an isocyanuric acid core with three substituents, each having allyl functional groups. The allyl functional groups provide positions for cross-linking with polymer chains. Varying the number and identity of the substituents on the isocyanurate compounds allows tuning of the number of available cross-linking positions. The number of positions at which cross-linking occurs affects the isocyanurate compounds' cross-linkability and flame retardancy.

Figure 1:
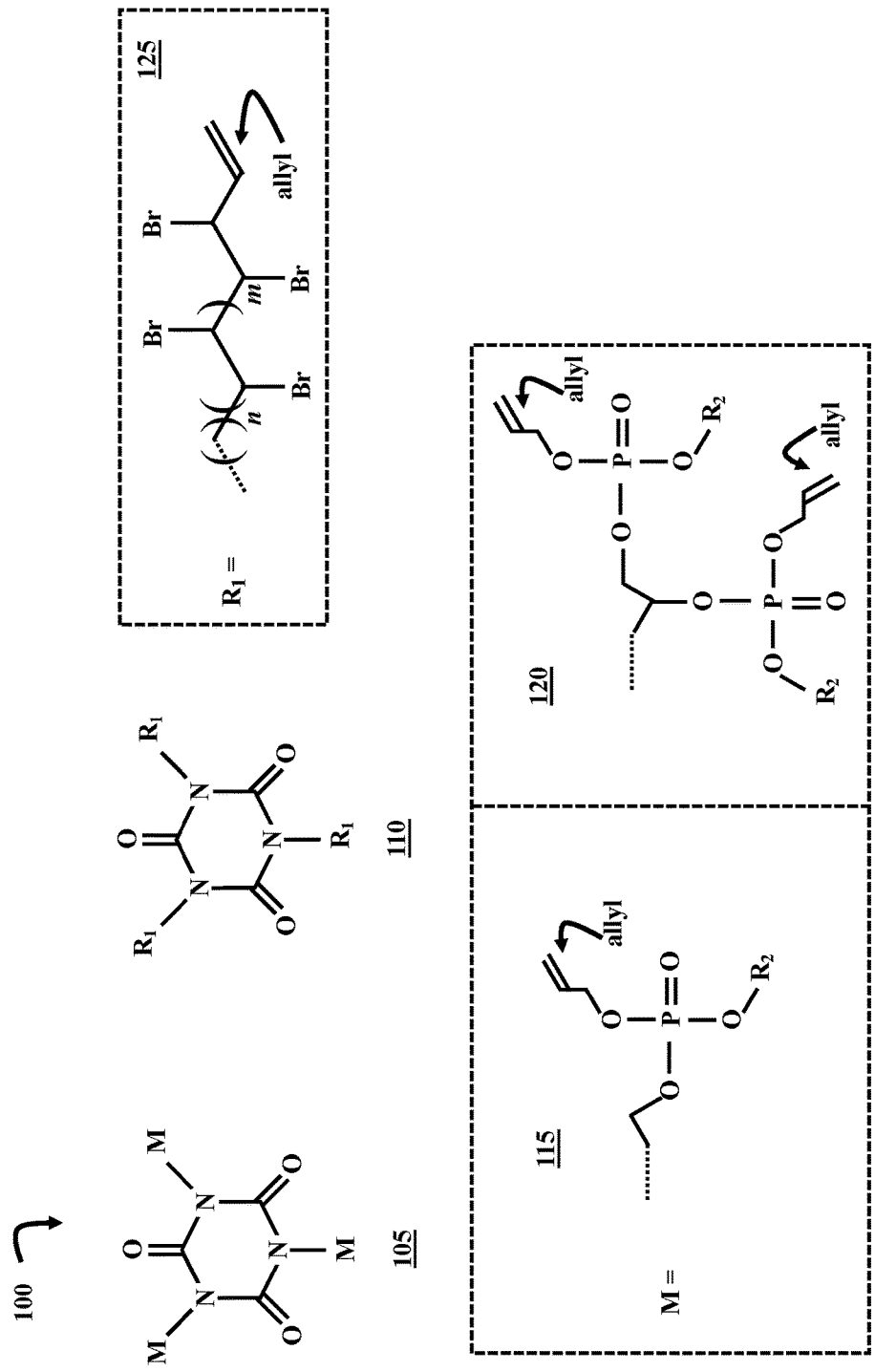
FIG. 1 is a diagrammatic representation of the molecular structures of a phosphate-based polyallyl isocyanurate compound and a brominated polyalkenyl isocyanurate compound, according to some embodiments of the present disclosure.

FIG. 1 is a diagrammatic representation of the molecular structures 100 of a phosphate-based polyallyl isocyanurate compound 105 and a brominated polyalkenyl isocyanurate compound 110. The phosphate-based polyallyl isocyanurate compound 105 has three allyl phosphate M substituents 115 or 120, and the brominated polyalkenyl isocyanurate compound 110 has three brominated alkene-terminated $R_1$ substituents 125. Though only one $R_1$ substituent 125 is illustrated in FIG. 1, the brominated polyalkenyl isocyanurate compound 110 can have alternative $R_1$ substituents, which are discussed with regard to FIGS. 5A and 5B. The two examples of potential M substituents 115 and 120 shown in FIG. 1 each have an $R_2$ group, in addition to their allyl functional groups. The $R_2$ group can also be an allyl, or it can be a different functional group, examples of which are discussed with regard to FIG. 3.

Figure 2A:
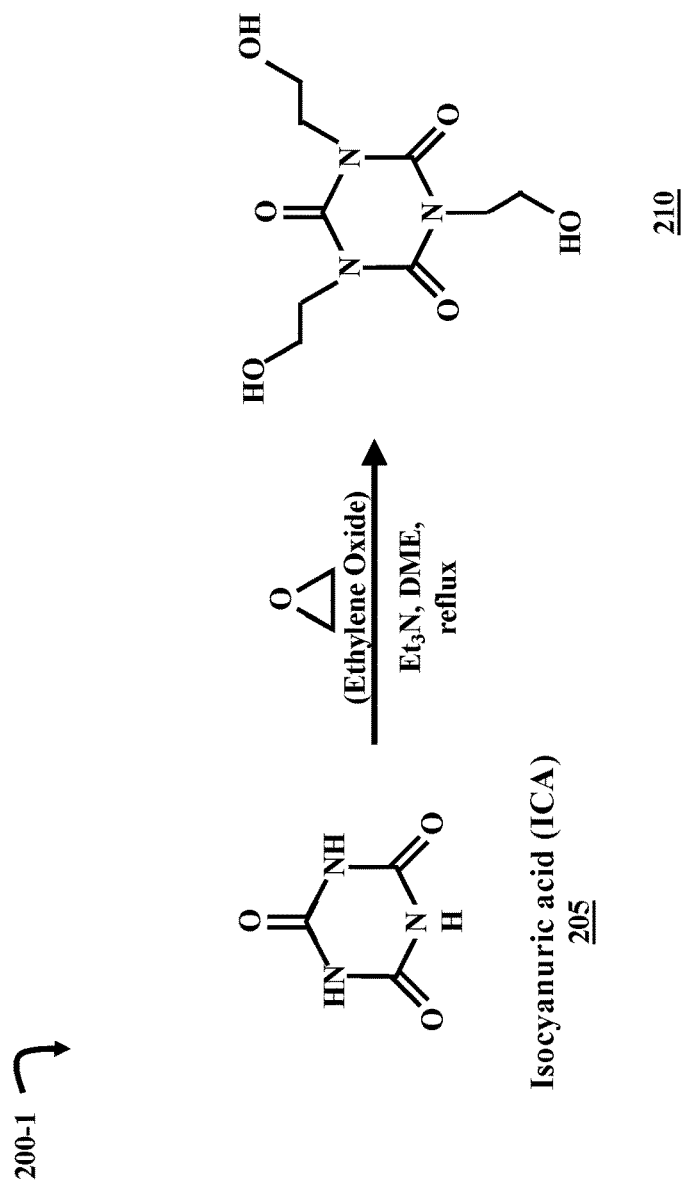
FIG. 2A is a chemical reaction diagram illustrating a process of synthesizing a trihydroxylated isocyanurate compound, according to some embodiments of the present disclosure.

FIG. 2A is a chemical reaction diagram illustrating a process 200-1 of synthesizing a trihydroxylated isocyanurate compound 210. The phosphate-based polyallyl isocyanurate compound 105 and other phosphate-based polyallyl isocyanurate compounds are derived from hydroxylated isocyanurate compounds, as is discussed in greater detail below. In process 200-1, isocyanuric acid (ICA) 205 in an organic solvent, such as dimethoxyethane (DME) or 2-methoxyethanol, is added to an organic base. The organic base shown in FIG. 2A is triethylamine ($Et_3N$), but triethyl benzyl ammonium chloride (TEBAC) or trienyl phosphine can also be used. The reaction mixture is refluxed under an atmosphere of ethylene oxide (approximately 2.5 atm). The reaction mixture is then poured into water, and the aqueous and organic layers are separated. The aqueous layer is extracted with ether, and rinsed with brine. The organic layer is dried over magnesium sulfate ($MgSO_4$), and the solvent is removed in vacuo. The trihydroxylated isocyanurate compound 210 residue is then purified by recrystallization or column chromatography. The trihydroxylated isocyanurate compound 210 is converted to a phosphate-based polyallyl isocyanurate compound 105 with M 115 substituents, as is illustrated in FIG. 3.

Figure 2B:
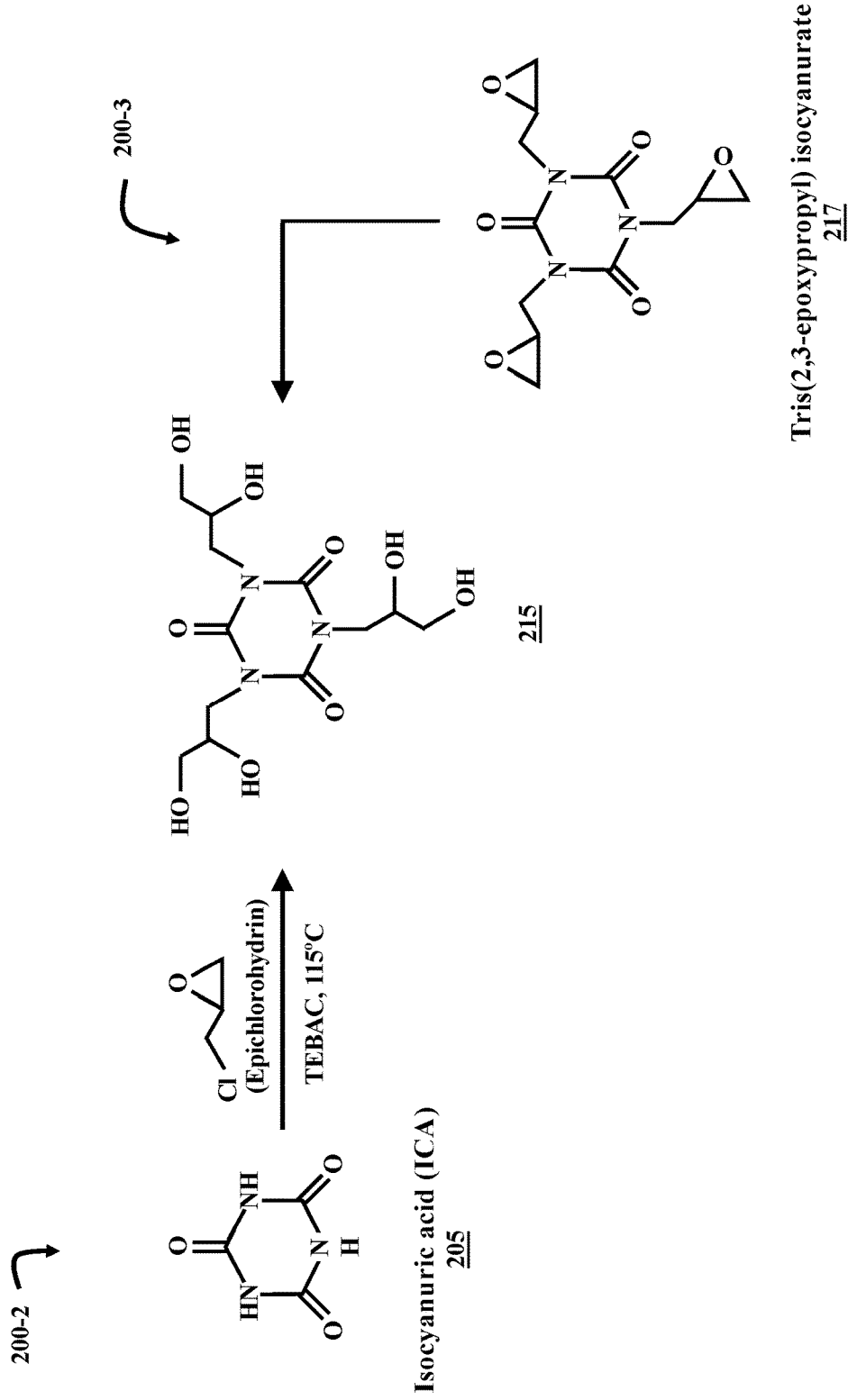
FIG. 2B is a chemical reaction diagram illustrating two processes of synthesizing a hexahydroxylated isocyanurate compound, according to some embodiments of the present disclosure.

FIG. 2B is a chemical reaction diagram illustrating two processes 200-2 and 200-3 of synthesizing a hexahydroxylated isocyanurate compound 215, according to one illustrative embodiment. The hexahydroxylated isocyanurate compound 215 is a precursor for a phosphate-based polyallyl isocyanurate compound 105 with M 120 substituents. In process 200-2, a mixture of isocyanuric acid (ICA), triethyl benzyl ammonium chloride (TEBAC), and epichlorohydrin is added to a reaction vessel fitted with a Dean-Stark condensation apparatus. The mixture is heated to approximately 115° C. and allowed to react at that temperature for approximately 5 hours. The reaction mixture is then cooled to approximately 45° C., and a 50 wt. % sodium hydroxide (NaOH) solution is added dropwise to the reaction mixture. The NaOH solution can optionally be added while the reaction is under reduced pressure. The reaction is neutralized with a hydrochloric acid (HCl) solution, and then extracted with ethyl acetate. The aqueous layer is extracted with ether, and then rinsed with brine. The organic layer is dried over magnesium sulfate ($MgSO_4$), and the solvent is removed in vacuo. The hexahydroxylated isocyanurate compound 215 residue can be purified by recrystallization or column chromatography. Other methods can be used to form the hexahydroxylated isocyanurate compound 215 as well. For example, in process 200-3, the hexahydroxylated isocyanurate compound 215 is derived from tris(2,3-epoxypropyl) isocyanurate 217.

Figure 3:
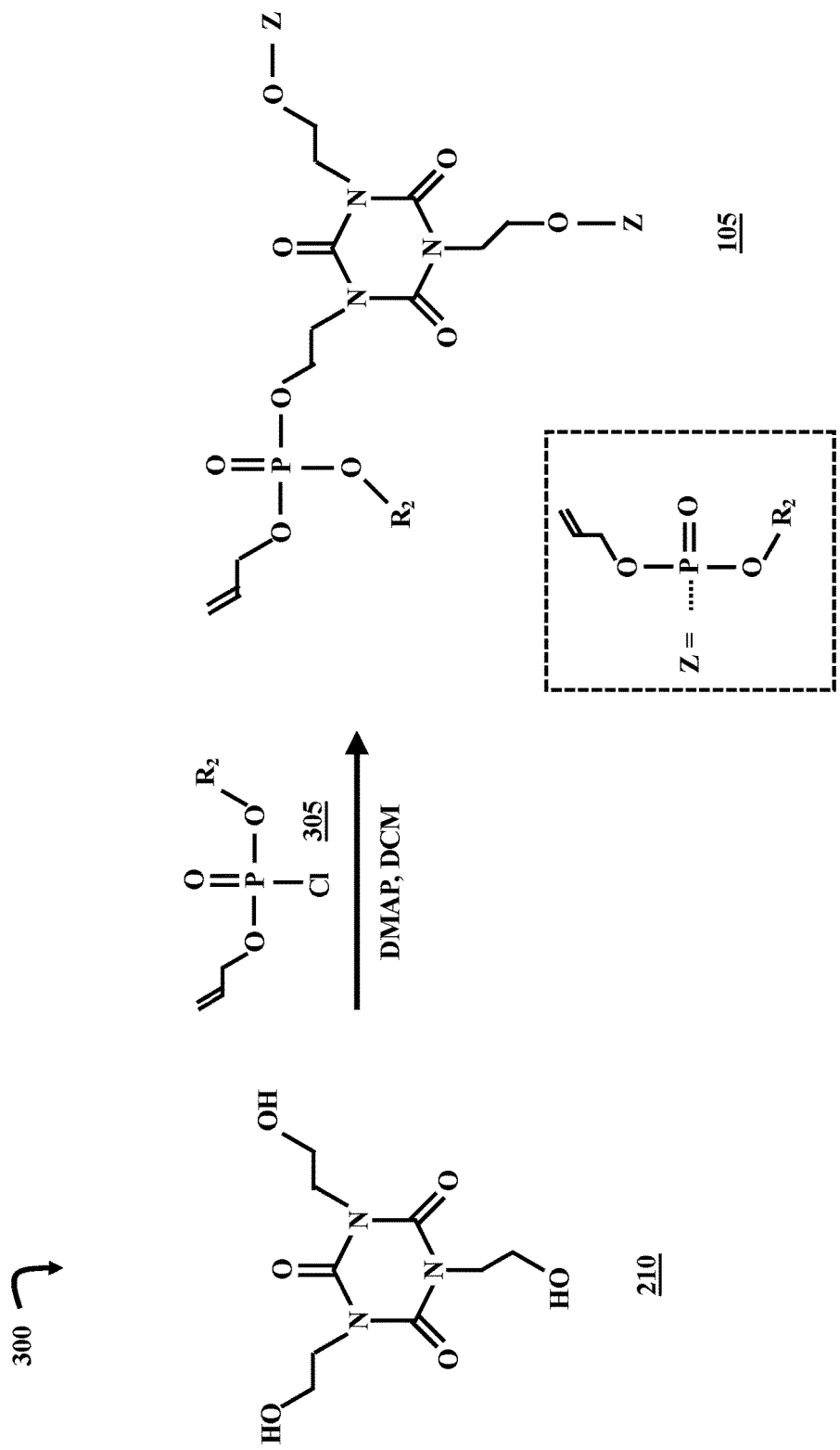
FIG. 3 is a chemical reaction diagram illustrating a process of synthesizing a phosphate-based polylallyl isocyanurate compound, according to some embodiments of the present disclosure.

FIG. 3 is a chemical reaction diagram illustrating a process 300 of synthesizing the phosphate-based polyallyl isocyanurate compound 105 from the trihydroxylated isocyanurate compound 210. In this prophetic example, the trihydroxylated isocyanurate compound 210 is combined with a catalytic amount (approximately 5 mol %) of dimethylaminopyridine (DMAP) under an atmosphere of inert gas (e.g., argon or nitrogen). The trihydroxylated isocyanurate compound 210 and DMAP are dissolved in an organic solvent such as dichloromethane (DCM), chloroform, tetrahydrofuran (THF), toluene, chlorobenzene, etc. Diallyl chlorophosphate is then added dropwise to the mixture. The reaction is carried out at or above room temperature, and can also be refluxed. The allyl chlorophosphate 305 has one allyl group and a second hydrocarbon functional group, $R_2$. In some embodiments, the hydrocarbon $R_2$ group is an additional allyl group, and, in other embodiments, the $R_2$ group is a hydrocarbon such as methyl, ethyl, propyl, isopropyl, phenyl, tolyl, anisolyl, benzyl, etc.

Hydrochloric acid (HCl) gas produced during process 300 is vented into a vessel containing an aqueous basic solution. In some embodiments, the reaction is carried out under reduced pressure in order to further drive the removal of HCl gas, promoting the reaction of diallyl chlorophosphate with the trihydroxylated isocyanurate compound 210. The reaction mixture is then added to a saturated aqueous solution of sodium bicarbonate ($NaHCO_3$), and the organic and aqueous layers are separated. The aqueous layer is extracted with ether, and rinsed with brine. The organic layer is dried over magnesium sulfate ($MgSO_4$), and the solvent is removed in vacuo. The phosphate-based polyallyl isocyanurate compound 105 residue can be purified by recrystallization or column chromatography.

Though process 300 is illustrated as involving the trihydroxylated isocyanurate compound 210, the reaction conditions of process 300 are general and can be applied to any reaction involving a hydroxylated isocyanurate compound and an alkene-terminated halophosphate. When process 300 begins with the trihydroxylated isocyanurate compound 210, the resulting phosphate-based polyallyl isocyanurate compound 105 has M 115 substituents, and when process 300 begins with the hexahydroxylated isocyanurate compound 215, the resulting phosphate-based polyallyl isocyanurate compound 105 has M 120 substituents. One difference between the M 115 and the M 120 substituents is that the M 120 substituents provide a greater number of possible cross-linking positions than the M 115 substituents.

In FIG. 3, the phosphate-based polyallyl isocyanurate compound 105 is illustrated as having three allyl phosphate Z substituents. The Z substituents can each have the same $R_2$ group, or they can have different $R_2$ groups. In cases where the $R_2$ groups are not identical to one another, the reaction can be carried out in multiple steps. Additionally, the phosphate-based polyallyl isocyanurate compound 105 can have Z substituents that are not illustrated in FIG. 3. These Z substituents can have allyl functional groups that provide cross-linking positions, but this is not necessarily the case. Examples of optional Z substituents that do not provide cross-linking positions include hydrocarbons, alkyl phosphates, aryl groups (e.g., phenyl), or mixtures of these. By varying the $R_2$ groups, the number of cross-linking positions on the substituted phosphate-based polyallyl isocyanurate compound 105 can be tuned.

Figure 4A:
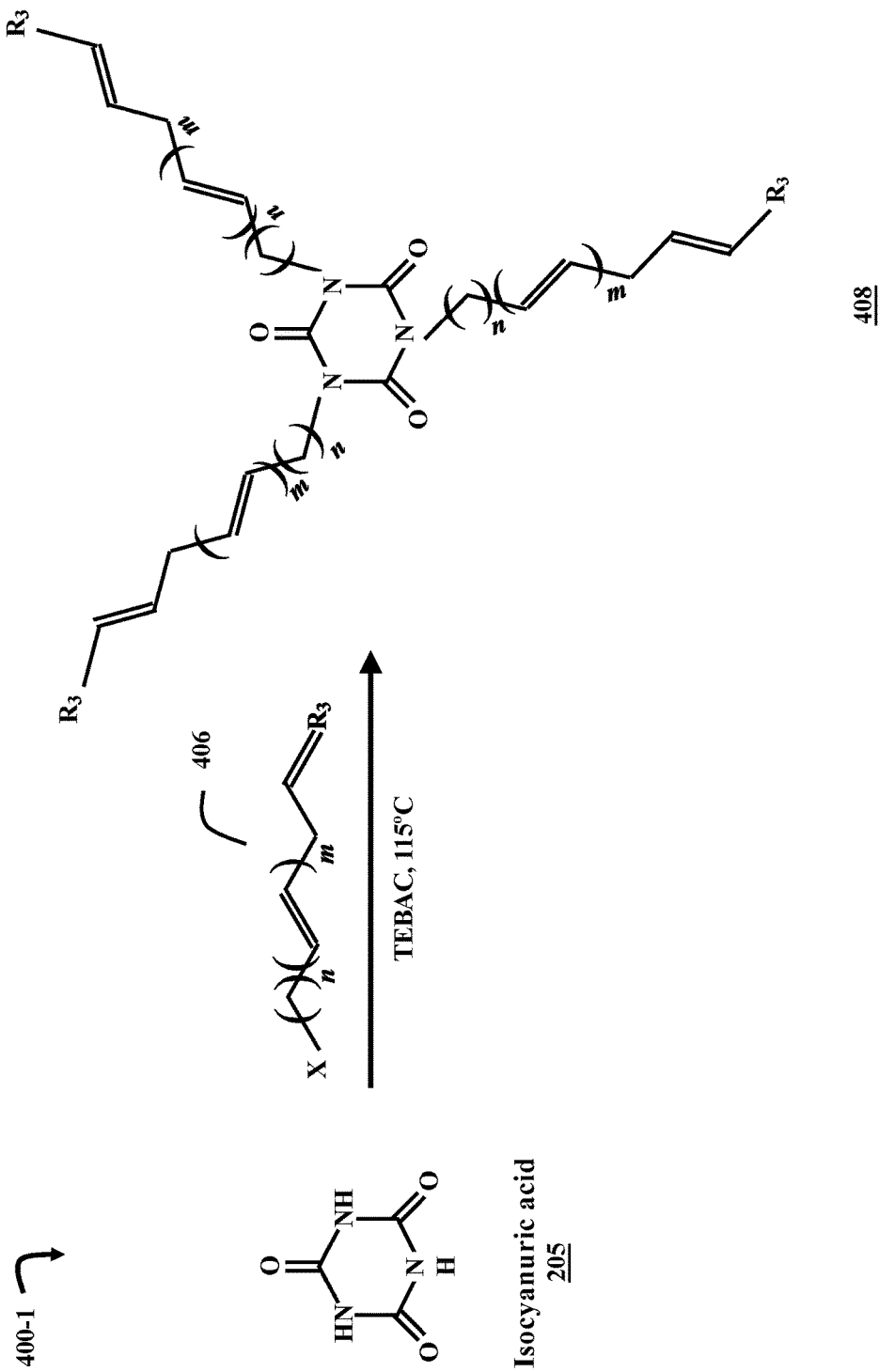
FIG. 4A is a chemical reaction diagram illustrating a process of synthesizing a vinylene isocyanurate compound, according to some embodiments of the present disclosure.

FIG. 4A is a chemical reaction diagram illustrating a process 400-1 of synthesizing a polyalkenyl isocyanurate compound 408. The polyalkenyl isocyanurate compound 408 is a precursor for the brominated polyalkenyl isocyanurate compound 110. The polyalkenyl isocyanurate compound 408 is formed in a reaction between isocyanuric acid 205 and an allylhalide 406. This reaction also involves a catalyst, TEBAC, and is carried out at approximately 115° C. In FIG. 4A, X represents a halide and $R_3$ represents an additional functional group. Examples of optional $R_3$ groups are discussed with respect to FIG. 4B. The allylhalide 406 can vary in the length of its aliphatic unit (n-block) and/or its vinylene unit (m-block).

Material properties of the cross-linking brominated polyalkenyl isocyanurate compound 110 derived from the vinylene isocyanurate compound 408 can be controlled by adjusting the length of the allylhalide 406. Examples of properties that can be controlled by altering the length of the aliphatic unit (n-block) include the glass transition temperature, crystallinity, tensile strength, and shear strength. Additionally, altering the length of the vinylene unit (m-block) allows the bromine content of the brominated polyalkenyl isocyanurate compound 110 to be adjusted, which can control the flame retardancy of the brominated polyalkenyl isocyanurate compound 110 and, consequently, the flame retardancy of the laminate resin.

Figure 4B:
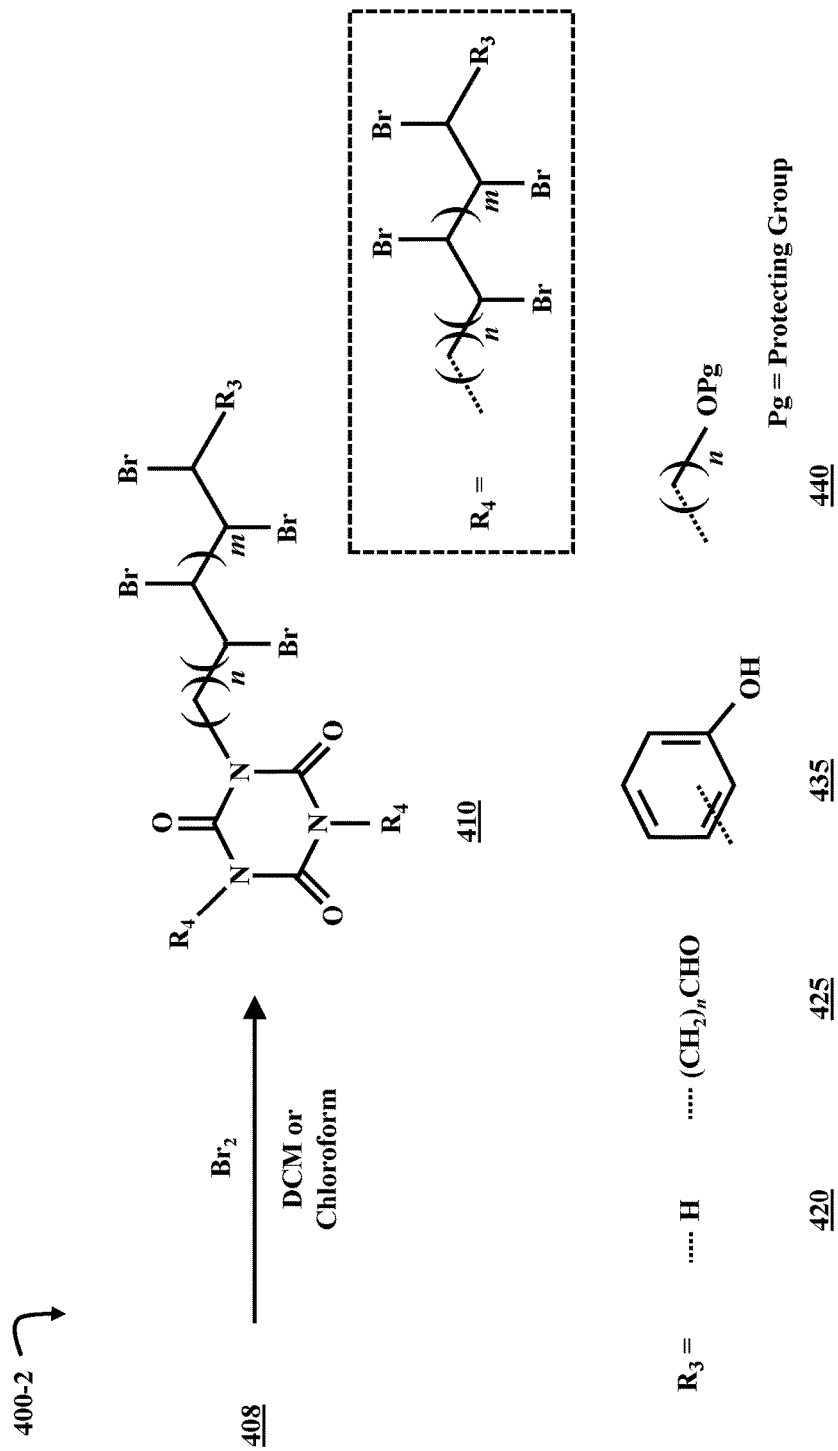
FIG. 4B is a chemical reaction diagram illustrating a process of synthesizing a brominated polyalkenyl isocyanurate precursor, according to some embodiments of the present disclosure.

FIG. 4B is a chemical reaction diagram illustrating a process 400-2 of synthesizing a brominated polyalkenyl isocyanurate precursor 410. In this reaction, the brominated polyalkenyl isocyanurate precursor 410 is produced in a reaction between the vinylene isocyanurate compound 408 and bromine ($Br_2$) in dichloromethane (DCM) or chloroform. The vinylene isocyanurate compound 408 is dissolved in dichloromethane or chloroform, and cooled by an ice bath. As the cooled solution is stirred, a dichloromethane or chloroform solution of bromine is added dropwise. The mixture is then stirred for approximately 2 hours at approximately 0° C. as a brominated polyalkenyl isocyanurate precursor 410 precipitate forms. The precipitate is filtered, and washed with petroleum ether. The brominated polyalkenyl isocyanurate precursor 410 residue is then purified by recrystallization.

The identity of the $R_3$ substituent on the brominated polyalkenyl isocyanurate precursor 410 directs the selection of a method for affixing a cross-linkable allyl functional group. Examples of possible $R_3$ groups include a hydrogen atom 420, $(CH_2)_n CHO$ (a linear aldehyde) 425, a phenol 435, and $CH_3(CH_2)_n OPg$ 440, where Pg refers to a protecting group. Examples of protecting groups include trialkylsilyl, benzyl, and cyclic ether (e.g., tetrahydropyran) protecting groups. Methods for affixing cross-linkable allyl functional groups to the brominated polyalkenyl isocyanurate precursor 410, and producing the brominated polyalkenyl isocyanurate compound 110, are discussed with respect to FIGS. 5A and 5B.

Figure 5A:
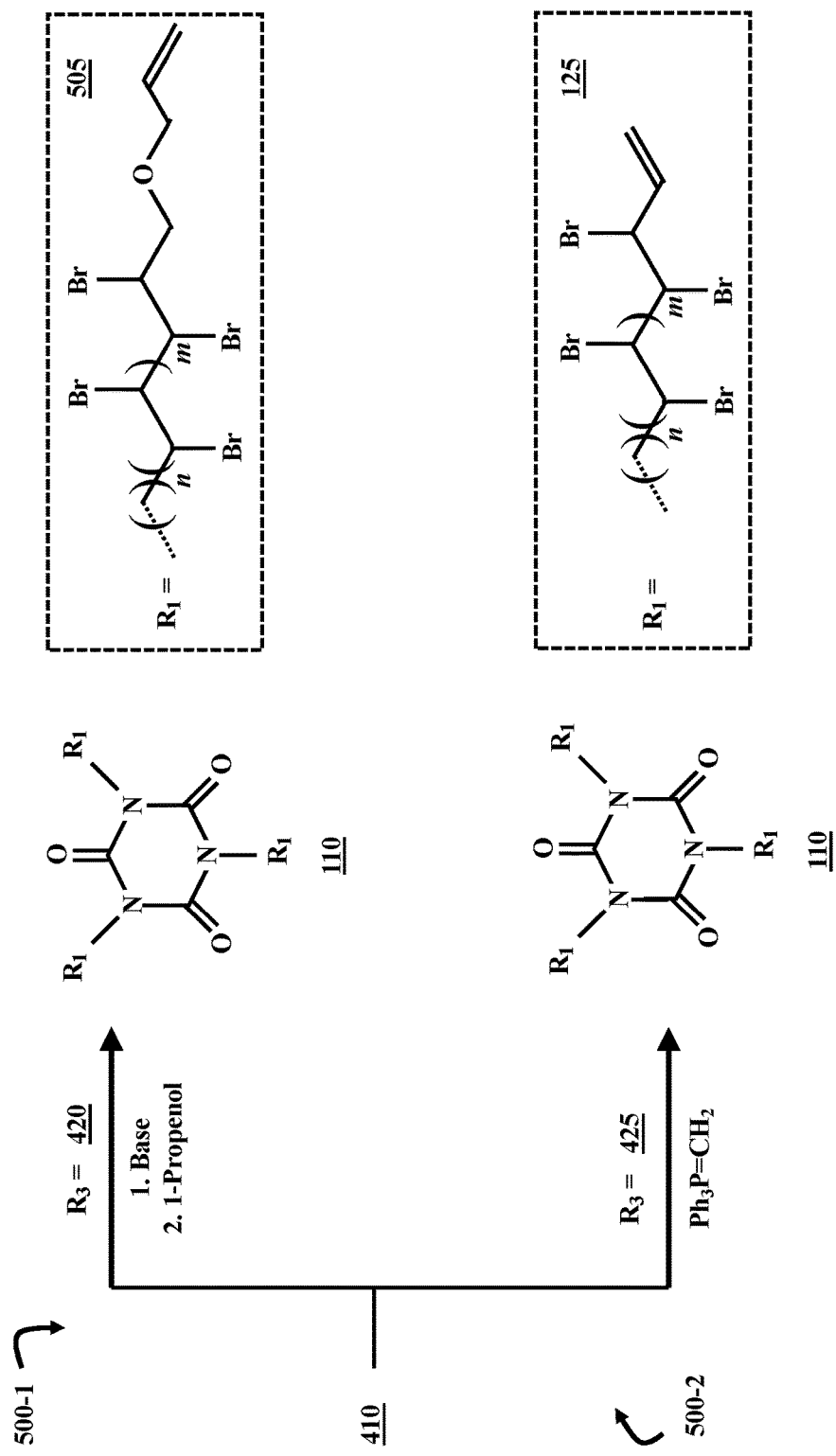
FIG. 5A is a first chemical reaction diagram illustrating processes of forming a brominated polyalkenyl isocyanurate compound, according to some embodiments of the present disclosure.

FIG. 5A is a chemical reaction diagram illustrating two processes 500-1 and 500-2 of forming a brominated polyalkenyl isocyanurate compound 110. In these processes, a brominated polyalkenyl isocyanurate precursor 410 is reacted under conditions that correspond to its $R_3$ substituent, thereby forming brominated polyalkenyl isocyanurate compounds 110 with varying $R_1$ substituents 505, 125, 515, and 520. In process 500-1, the $R_3$ substituent on the brominated polyalkenyl isocyanurate precursor 410 is a hydrogen atom 420. The brominated polyalkenyl isocyanurate precursor 410 is added to a mixture of 1-propenol and a base (e.g., sodium hydride). The mixture is dissolved in an organic solvent, such as tetrahydrofuran (THF) or ether. The reaction mixture is stirred for approximately 3 hours, and then neutralized by hydrochloric (HCl) acid. The aqueous and organic layers are then separated. The aqueous layer is extracted with diethyl ether, and rinsed with brine. The organic layer is dried over magnesium sulfate ($MgSO_4$), and the solvent is removed in vacuo. The residue is purified by recrystallization or column chromatography, yielding a brominated polyalkenyl isocyanurate compound 110 with a cross-linkable allyl functional group on its $R_1$ substituent 505.

In process 500-2, the $R_3$ substituent on the brominated polyalkenyl isocyanurate precursor 410 is a linear aldehyde 425. The brominated polyalkenyl isocyanurate precursor 410 is added to a solution of methylene triphenylphosphorane ($Ph_3P=CH_2$). In some embodiments, the methylene triphenylphosphorane is generated in situ by a reaction between bromomethane and triphenyl phosphine, followed by deprotonation. The brominated polyalkenyl isocyanurate precursor 410 and triphenylphosphorane mixture is stirred for approximately 18 hours at approximately 120° C., and then neutralized by an aqueous hydrochloric acid (HCl) solution. The aqueous and organic layers are separated, and the aqueous layer is extracted with diethyl ether and rinsed with brine. The organic layer is dried over magnesium sulfate ($MgSO_4$), and the solvent is removed in vacuo. The residue is purified by recrystallization or column chromatography, yielding a brominated polyalkenyl isocyanurate compound 110 with a cross-linkable allyl functional group on its $R_1$ substituent 125.

Figure 5B:
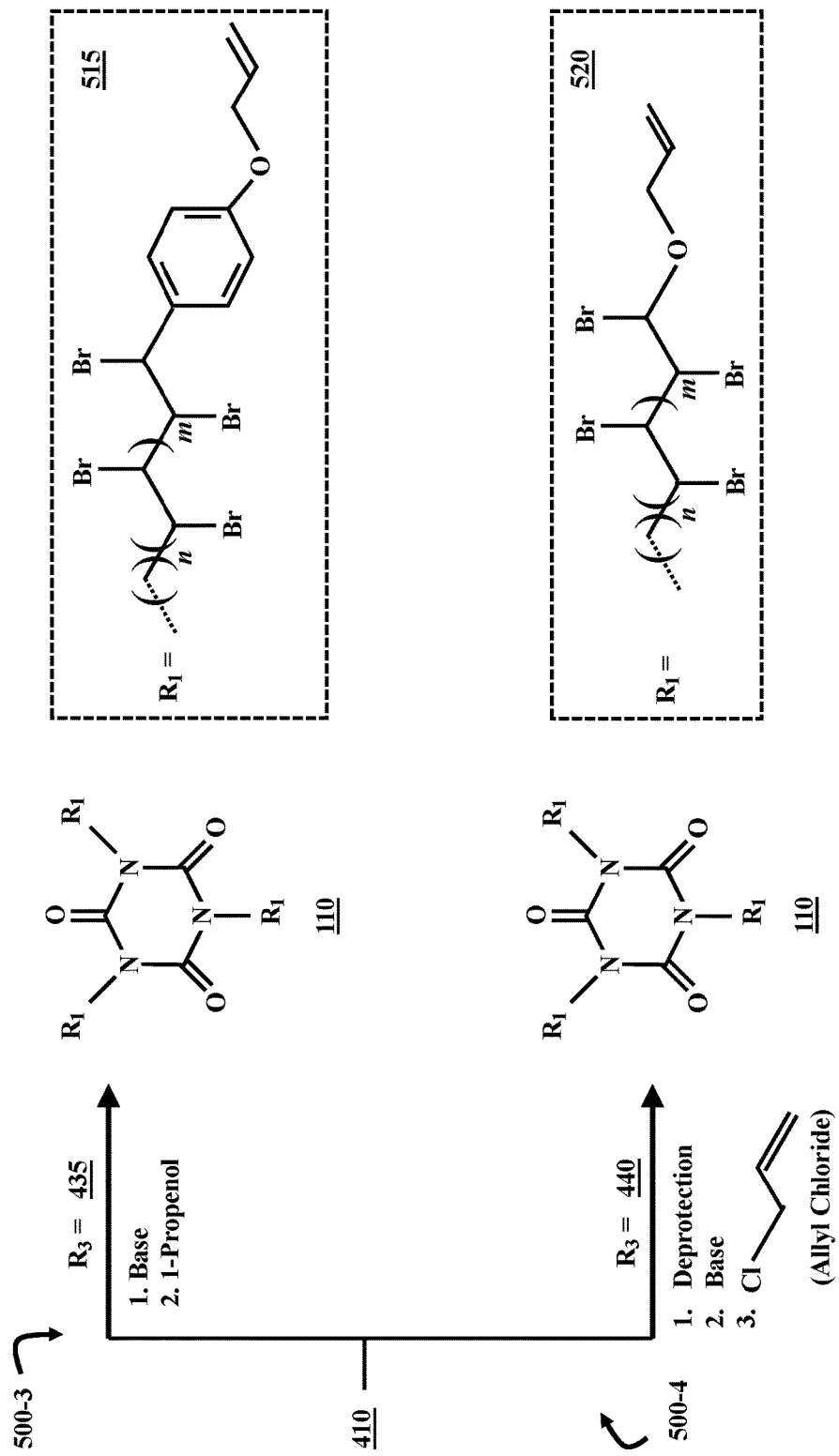
FIG. 5B is a second chemical reaction diagram illustrating processes of forming a brominated polyalkenyl isocyanurate compound, according to some embodiments of the present disclosure.

FIG. 5B is a chemical reaction diagram illustrating processes 500-3 and 500-4 of forming a brominated polyalkenyl isocyanurate compound 110. In process 500-3, the $R_3$ functional group on the brominated polyalkenyl isocyanurate precursor 410 is a phenol 435. The phenol group 435 can be bound to the brominated polyalkenyl isocyanurate precursor 410 at any carbon atom, as is indicated by the placement of the dashed line symbolizing the phenol isocyanurate bond in FIG. 4B. The hydroxyl group of the phenol 435 is deprotonated in a reaction with a base. The proton is substituted by 1-propenol, forming a brominated polyalkenyl isocyanurate compound 110 with an $R_1$ substituent 515 that has a cross-linkable allyl functional group.

In process 500-4, the $R_3$ substituent of the brominated polyalkenyl isocyanurate precursor 410 is $CH_3(CH_2)_n OPg$ 440, a deprotonated alcohol with a protecting group (Pg). The brominated polyalkenyl isocyanurate precursor 410 is reacted with a base (e.g., sodium hydride) after removal of the protecting group. The deprotected brominated polyalkenyl isocyanurate precursor 410 is then reacted with allyl chloride, or another allyl halide, in an organic solvent such as tetrahydrofuran (THF) or ether. The reaction mixture is stirred for approximately 30 minutes, and then neutralized with an aqueous solution of hydrochloric (HCl) acid. The aqueous and organic layers are separated, and the aqueous layer is extracted with diethyl ether, and rinsed with brine. The organic layer is dried over magnesium sulfate ($MgSO_4$), and the solvent is removed in vacuo. The residue is purified by recrystallization or column chromatography, yielding the brominated polyalkenyl isocyanurate compound 110 with a cross-linkable allyl functional group on its $R_1$ substituent 520.

In some embodiments, the brominated polyalkenyl isocyanurate compound 110 or the phosphate-based polyallyl isocyanurate compound 105 of the present disclosure are combined, as a cross-linker, with a polymer in order to form a resin that can be incorporated into laminates for printed circuit board (PCB) construction. A laminate also has a fiber such as paper, phenol cotton paper, carbon fiber, fiberglass, etc. The polymer can be any polymer with an organic functional group capable of forming a link with a vinyl functional group. Examples of polymers that can form links with vinyl functional groups include epoxide polymers, such as poly(p-phenylene oxide) and vinylbenzene-terminated poly(phenyleneoxide), and acrylate polymers, such as methyl methacrylate.

It should be noted that, in some embodiments, the compounds described herein can contain one or more chiral centers. These can include racemic mixtures, diastereomers, enantiomers, and mixtures containing one or more stereoisomer. Further, the disclosed can encompass racemic forms of the compounds in addition to individual stereoisomers, as well as mixtures containing any of these.

The synthetic processes discussed herein and their accompanying drawings are prophetic examples, and are not limiting; they can vary in reaction conditions, components, methods, etc. In addition, the reaction conditions can optionally be changed over the course of a process. Further, in some embodiments, processes can be added or omitted while still remaining within the scope of the disclosure, as will be understood by a person of ordinary skill in the art.

What is claimed is:

1. A flame-retardant resin in a printed circuit board laminate, the flame-retardant resin comprising:

a polymer selected from a group consisting of an epoxide polymer, an acrylate polymer, a poly(p-phenylene oxide) polymer, and a methyl methacrylate polymer; and a cross-linker compound selected from a group consisting of a flame-retardant phosphate-based polyallyl isocyanurate cross-linker compound, a flame-retardant polyalkenyl isocyanurate cross-linker compound, and a flame-retardant brominated polyalkenyl isocyanurate cross-linker compound, wherein the flame-retardant phosphate-based polyallyl isocyanurate cross-linker compound and the flame-retardant polyalkenyl isocyanurate cross-linker compound each have a formula of:

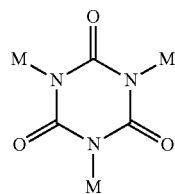

wherein each of M is a phosphate-based substituent selected from a group consisting of a substituent with a formula of:

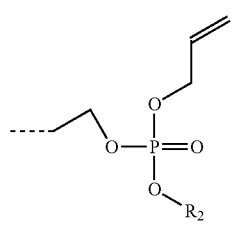

and a substituent with a formula of:

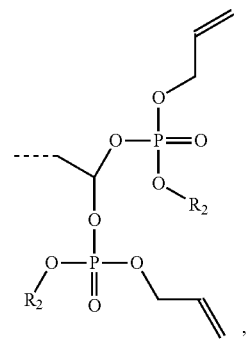

wherein $R_2$ is a functional group selected from a group consisting of an allyl, a methyl, an ethyl, a propyl, an isopropyl, a phenyl, a tolyl, an anisolyl, and a benzyl, and wherein the flame-retardant brominated polyalkenyl isocyanurate cross-linker compound has a formula of:

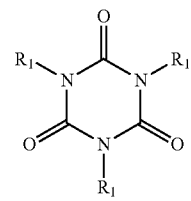

wherein each of $R_1$ is a brominated alkene-terminated substituent selected from a group consisting of a brominated alkene-terminated substituent with a formula of:

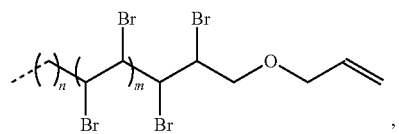

a brominated alkene-terminated substituent with a formula of:

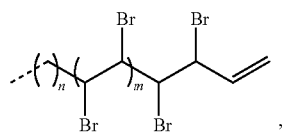

a brominated allyl substituent with a formula of:

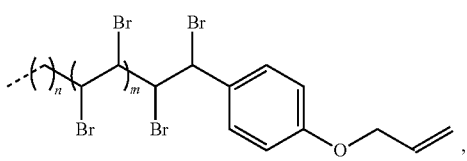

and
a brominated allyl substituent with a formula of:

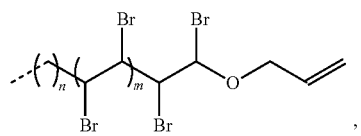

wherein n is a first number of repeating units, and m is a second number of repeating units.

2. A flame-retardant resin in a printed circuit board laminate, the flame-retardant resin comprising:
a polymer selected from a group consisting of an epoxide polymer, an acrylate polymer, a poly(p-phenylene oxide) polymer, and a methyl methacrylate polymer; and
a cross-linker compound selected from a group consisting of a flame-retardant phosphate-based polyallyl isocyanurate cross-linker compound and a flame-retardant polyalkenyl isocyanurate cross-linker compound, wherein the flame-retardant phosphate-based polyallyl isocyanurate cross-linker compound and the flame-retardant polyalkenyl isocyanurate cross-linker compound each have a formula of:

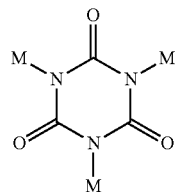

wherein each of M is a phosphate-based substituent selected from a group consisting of a substituent with a formula of:

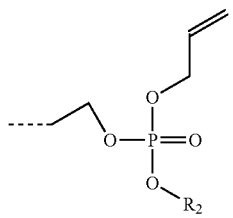

and a substituent with a formula of:

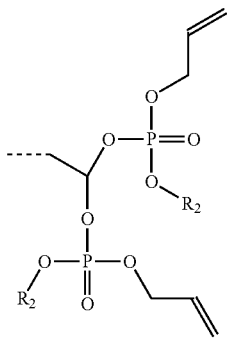

wherein $R_2$ is a functional group selected from a group consisting of an allyl, a methyl, an ethyl, a propyl, an isopropyl, a phenyl, a tolyl, an anisolyl, and a benzyl.

* * * * *